United States Patent [19]

Hossain

[11] Patent Number: 6,043,486
[45] Date of Patent: Mar. 28, 2000

[54] ABSOLUTE STANDARD REFERENCE MATERIALS FOR LOW-LEVEL CONCENTRATION MEASUREMENTS

[75] Inventor: Tim Z. Hossain, Austin, Tex.

[73] Assignee: Advanced Micro Devices, Inc., Sunnyvale, Calif.

[21] Appl. No.: 09/225,396

[22] Filed: Jan. 5, 1999

Related U.S. Application Data

[62] Division of application No. 08/712,716, Sep. 12, 1996, Pat. No. 5,866,899.

[51] Int. Cl.[7] .................................................. G01N 33/00
[52] U.S. Cl. ........................ 250/252.1; 250/303; 378/45; 378/48; 378/207; 436/57
[58] Field of Search ............................... 250/252.1, 303; 378/45, 48, 207; 436/57

[56] References Cited

U.S. PATENT DOCUMENTS

| | | |
|---|---|---|
| 3,064,130 | 11/1962 | Di Lanni et al. . |
| 3,107,299 | 10/1963 | Jachter . |
| 3,519,821 | 7/1970 | Bolster . |
| 3,751,661 | 8/1973 | Packer et al. . |
| 3,859,179 | 1/1975 | Staples . |
| 4,092,539 | 5/1978 | Pao et al. . |
| 4,119,847 | 10/1978 | Waggoner . |
| 4,256,960 | 3/1981 | Snider . |
| 4,270,052 | 5/1981 | King . |
| 4,406,947 | 9/1983 | Burton et al. . |

(List continued on next page.)

FOREIGN PATENT DOCUMENTS

| | | |
|---|---|---|
| 59-116533 | 5/1984 | Japan . |
| 60-135842 | 7/1985 | Japan . |
| 6-148337 | 5/1994 | Japan . |
| 1146-091 | 1/1984 | U.S.S.R. . |
| 1469-402 | 4/1987 | U.S.S.R. . |
| 984834 | 3/1965 | United Kingdom . |

OTHER PUBLICATIONS

"Automatic Calibration of Radiation Monitoring Films" Abstract, UKAEA Res. Group; AERE, Harwell, Berks., England; Report No. AERE–R6037; (1969).

John Volpe, "Bettis Reactor Engineering School Nuclear Physics Notes", Rev. 1; Topic 8—Radioactivity, pp. 8–1 to 8–8.

R.S. Hockett, TXRF Detection of Subsurface Metals in Silicon Substrates, in the Proceedings of the Symposium on *Diagnostic Techniques for Semiconductor Materials and Devices*, vol. 92–2, pp. 132–139.

Patent Abstracts of Japan Grp P1598, vol. 17, No. 461, Abs. p–6, dated Aug. 23, 1993 (05–107388) Ueda et al. "Method for Measuring Neutron Effective Multiplication Constant During Storage of Radiation Fuel."

(List continued on next page.)

*Primary Examiner*—Constantine Hannaher
*Assistant Examiner*—Andrew Israel
*Attorney, Agent, or Firm*—Skjerven, Morrill, MacPherson, Franklin & Friel LLP

[57] ABSTRACT

A concentration measurement device is calibrated for a target element by performing a concentration measurement on a reference standard sample which includes a number of atoms of a radioactive marker element in known ratio to a number of atoms of the target element. Both the ratio of atoms of the target element to those of the radioactive marker element and a count of decay products of the radioactive marker element are analytically quantified. Because the count of decay products is correlated with the number of atoms of the radioactive marker element, the ratio and the count of decay products are used to accurately calculate the otherwise unknown number of impurity atoms and to calibrate a concentration measurement signal from the concentration measurement device.

25 Claims, 3 Drawing Sheets

U.S. PATENT DOCUMENTS

| | | |
|---|---|---|
| 4,510,573 | 4/1985 | Boyce et al. . |
| 4,524,279 | 6/1985 | Christianson et al. . |
| 4,771,177 | 9/1988 | Brown . |
| 4,779,621 | 10/1988 | Mattson . |
| 4,912,323 | 3/1990 | Bhat et al. . |
| 4,985,906 | 1/1991 | Arnold . |
| 5,024,801 | 6/1991 | Impink, Jr. et al. . |
| 5,164,093 | 11/1992 | Chilton et al. . |
| 5,210,778 | 5/1993 | Massart . |
| 5,373,544 | 12/1994 | Goebel . |
| 5,376,803 | 12/1994 | McFee et al. . |
| 5,497,407 | 3/1996 | Komatsu et al. . |
| 5,559,324 | 9/1996 | Rapkin et al. . |
| 5,637,506 | 6/1997 | Goken et al. . |
| 5,760,394 | 6/1998 | Welle .................................. 250/303 |

OTHER PUBLICATIONS

*Minutes of ISO/TC201/WG2 on Total Reflection X–Ray Fluorescence Spectroscopy*, ISO/TC 201/WG2 N 27, Jan. 29, 1996.

Third Working Draft, Surface Chemical Analysis—Determination Of Contamination Elements Contents On Silicone Wafer—Total Reflections X–Ray Fluorescence Spectroscopy (TXRF), ISO/TC 201/WG2 N 26, Nov. 27, 1995.

R. S. Hockett, Proceedings from the Denver X–Ray Conference, *An Update on Standards Activity for TXRF and the Challenges Ahead*, Aug. 1995, pp. 1–4.

ABSOLUTE STANDARD REFERENCE MATERIALS FOR LOW-LEVEL CONCENTRATION MEASUREMENTS

This application is a division of Application Ser. No. 08/712,716, filed Sep. 12, 1996, now U.S. Pat. No. 5,866,899.

BACKGROUND OF THE INVENTION

1. Field of the Invention

The present invention relates to materials, methods, and systems for calibrating concentration measurements, and more particularly to materials, methods, and systems for calibrating surface impurity concentration measurements for semiconductor fabrication.

2. Description of the Related Art

Modern semiconductor fabrication techniques, including those for Very Large Scale Integration (VLSI), require extraordinary levels of cleanliness. In fact, reduction of trace contaminant levels is a primary goal of semiconductor fabrication and research facilities. Performance and yield are both adversely affected by trace impurity levels. Today, ultra-clean fabrication and research facilities demand surface contamination levels below $10^{10}$ atoms/cm$^2$ and future facilities will require levels below $10^9$ atoms/cm$^2$.

Consequently, the semiconductor industry, including researchers, wafer suppliers and device manufacturers, requires improved analytical techniques to measure organic and inorganic surface contaminants. Trace amounts of metallic contaminants are of particular concern and are known to seriously affect both performance and manufacturing yield of integrated circuits. To achieve the desired levels of cleanliness, extremely sensitive quantitative analysis techniques are required to measure impurity concentration levels. In turn, the equipment used in these techniques requires precise calibration. Examples of such quantitative analysis techniques include:

1. Total Reflection X-ray Fluorescence (TXRF), in which an X-ray beam strikes the surface to be examined at a grazing angle (below the "critical angle" or angle for total reflection) thus resulting in surface sensitivity of a few monolayers;
2. Time of Flight Secondary Ion Mass Spectroscopy (TOF-SIMS), in which surface impurity atoms are sputtered off by a pulsed ion beam and subsequently detected by a time of flight mass spectrometer; and
3. Heavy Ion Backscattering (HIBS), in which a high mass, moderate energy ion beam is backscattered by surface atoms, the characteristics of the backscattered ions depending on the species of the surface scatterer.

Calibration of each of these quantitative analysis techniques for low-level impurity concentrations has proved difficult.

In general, calibration of equipment used in quantitative analysis techniques is necessary because of the variety of factors that affect the measurement, such as background noise, variations in detector and collection efficiency, uncontrolled sources of contamination, and variations in response from the impurity. Unfortunately, precise calibration of surface contamination measurement equipment typically requires the preparation of a tightly controlled reference standard with a precisely known impurity level. In this way, the actual response of the equipment can be calibrated against the known impurity level of a reference standard. Because it is difficult to precisely control the number of impurity atoms deposited on a reference standard, powerful analytical techniques have been used to characterize the reference standard before the reference standard can, itself, be used to calibrate other measurement equipment. For example, standards used for calibrating TXRF equipment have first been characterized by other methods, such as Atomic Absorption Spectrometry (AAS) or Inductively Coupled Plasma Mass Spectrometry ICP-MS. Unfortunately, many of these techniques suffer from their own calibration problems and from a similar lack of reference standards at concentration levels at or below $10^{10}$ atoms/cm$^2$. As a result, precise calibration standards for surface concentration measurements in the range now desired (i.e., at or below $10^{10}$ atoms/cm$^2$) are not generally available.

The problems inherent in many current calibration techniques can be illustrated in the context of TXRF, which is commonly used in the semiconductor industry to monitor the level of surface contamination on wafers at various stages of device fabrication. In order to provide a quantitative measurement of surface contamination levels, calibration curves have been measured based on well controlled standard samples with known impurity concentration. However, current calibration techniques have proved unreliable at surface contamination levels on the order of $10^{10}$ atoms/cm$^2$. Round-robin measurements have been used with only marginal success in an attempt to mask inconsistencies among characterizations of reference standards. For example, round-robin test results reported to the ISO/TC 201/WG2 on Total X-ray Fluorescence Spectroscopy indicated inconsistencies in calibration data measured by a variety of different researchers despite the fact that they were using the same method. See e.g., *Third Working Draft, Surface chemical analysis—Determination of contamination elements contents on silicone wafer—Total reflections X-ray fluorescence spectroscopy (TXRF)*, ISO/TC 201/WG2 N 26, Nov. 28, 1995. Chief among the report's concerns were the accuracy of initial measurements of the impurity concentration and unintended contamination from external sources. These problems are compounded when contamination takes the form of the same impurity atom intentionally used in the standard, or when the originally known contamination levels decrease unpredictably. Annex C of the above report specifies compositions for, procedures for preparing, and methods for calibrating a TXRF measurement apparatus with a standard specimen.

SUMMARY OF THE INVENTION

It has been discovered that a concentration measurement device can be calibrated for a target element by performing a concentration measurement on a reference standard sample which includes a number of atoms of a radioactive marker element in known ratio to a number of atoms of the target element. Both the ratio of atoms of the target element to those of the radioactive marker element and a count of decay products of the radioactive marker element are analytically quantified. Because the count of decay products is correlated with the number of atoms of the radioactive marker element, the ratio and the count of decay products are used to accurately calculate the otherwise unknown number of impurity atoms and to calibrate a concentration measurement signal from the concentration measurement device.

In one embodiment of the present invention, a reference standard sample includes a target element Fe mixed with an Fe-55 radioactive marker at a ratio of 1000:1 (atomic) deposited on a Si wafer with a spot size of approximately 1 mm in diameter. In another embodiment of the present invention, a calibration system includes a Si(Li) X-ray detector and a TXRF instrument, each with associated electronic processing of X-ray signals from the reference standard sample. In yet another embodiment of the present invention, a method for calibrating a concentration measurement includes preparing a stock solution of Fe and Fe-55 at a ratio of 1000:1 (mass), depositing a drop of the stock solution on a Si wafer, measuring the Fe-55 X-ray decay product count rate with a Si(Li) detector, and accurately determining the Fe:Fe-55 ratio using a TOF-SIMS system.

Various alternative embodiments include alternative selections of the target element and the radioactive marker element, including selections in which radioactive marker element is, and is not, an isotope of the target element, and including radioactive marker element selections having short half-lives (ranging from approximately 1–2 hours to approximately 5–10 days) and having longer half-lives (up to approximately 10 years).

In still yet another embodiment of the present invention, a reference standard material for calibrating a concentration measurement apparatus includes a substrate, a first amount of a target element detectable by the concentration measurement apparatus and on the substrate, and a second amount of a radioactive marker element combined with the target element on the substrate in known ratio.

In still yet another embodiment of the present invention, a method for calibrating a concentration measurement apparatus using a reference standard material includes the steps of providing a reference standard sample, measuring a flux of radioactive decay products, measuring a concentration of the target element, and calculating a calibration adjustment. The reference standard sample provided includes a first amount of a target element and a second amount of a radioactive marker element combined with the target element. The radioactive marker element has a known half-life. The flux of radioactive decay products is measured from the reference standard material. The concentration of the target element is measured using the concentration measurement apparatus. The calibration adjustment is calculated as an adjustment to the concentration measured in the concentration measuring step and is calculated using a known ratio of first and second amounts, the known half-life of the radioactive marker element, and the radioactive decay product flux measured in the flux measuring step.

In still yet another embodiment of the present invention, a method for characterizing a reference standard sample as a calibration standard for a concentration measurement apparatus, wherein the reference standard sample includes a target element and a radioactive marker element, includes the steps of measuring a flux of radioactive decay products from the radioactive marker element, calculating a concentration of the radioactive marker element, determining a ratio of the target element to the radioactive marker element, and supplying as a reference standard sample characterization an indication of target element concentration. The concentration calculation is in accordance with radioactive decay equations uses a known half-life of the radioactive marker element and the measured radioactive decay product flux.

In still yet another embodiment of the present invention, an apparatus includes a surface concentration measurement apparatus and a calibration subsystem. The surface concentration measurement apparatus has a detector for generating a first signal indicative of a surface concentration measurement of a target element on a reference standard sample. The calibration subsystem is coupled to receive the first signal and to supply a calibration correction of the first signal using a predetermined ratio of amounts of the target element and a radioactive marker element. The calibration subsystem supplies the calibration correction using a radioactive decay product measurement indicative of the amount of the radioactive marker element on the reference standard sample.

BRIEF DESCRIPTION OF THE DRAWINGS

The present invention may be better understood, and its numerous objects, features, and advantages made apparent to persons of ordinary skill in the art by referencing the accompanying drawings.

The use of the same reference symbols in different drawings indicates similar or identical items.

DETAILED DESCRIPTION OF THE PREFERRED EMBODIMENTS

Figure 1:
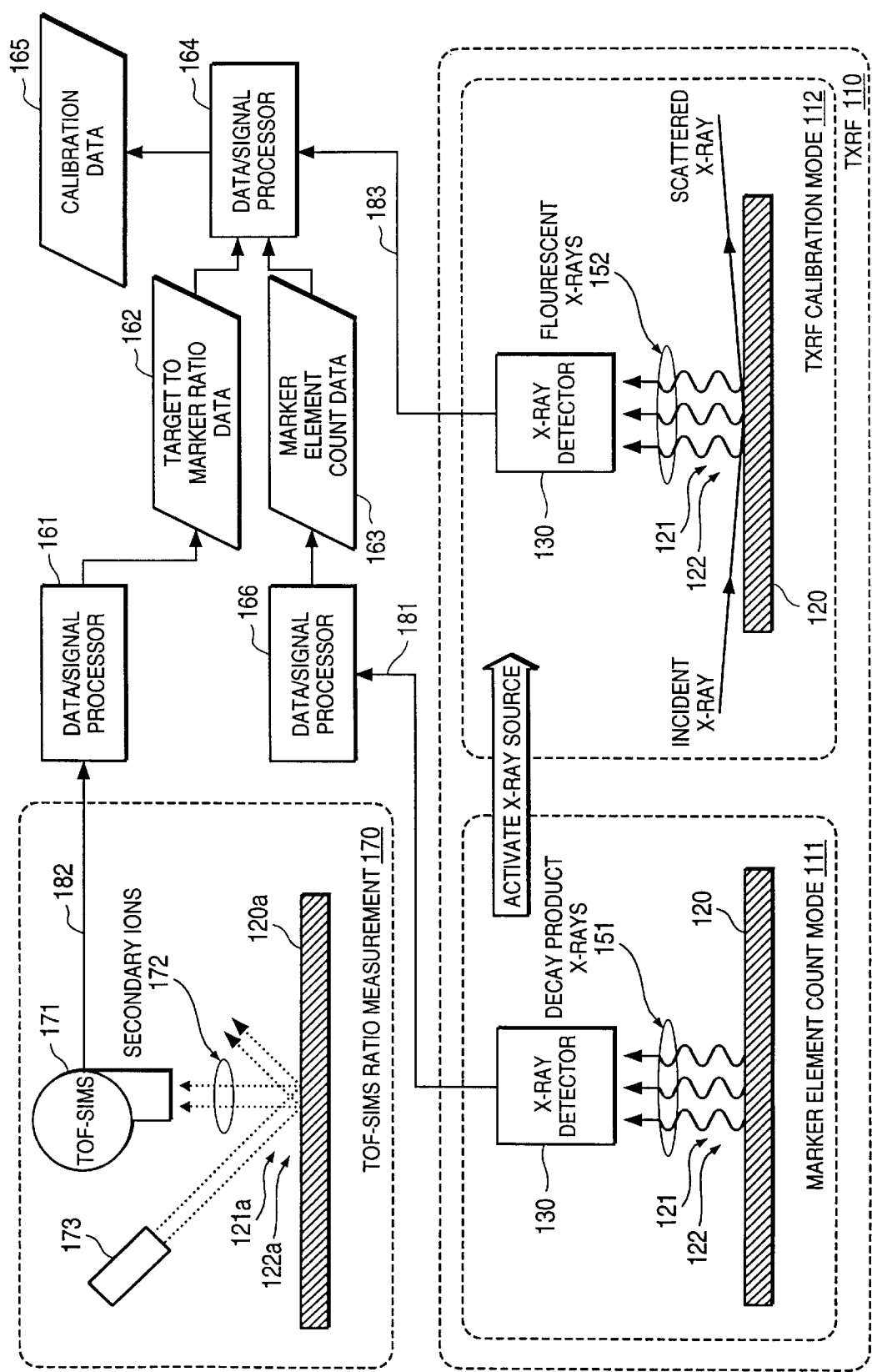
FIG. 1 depicts a system, apparatus, and method for calibrating a Total X-Ray Fluorescence (TXRF) apparatus for low-level surface concentration measurements using a reference standard sample in accordance with an exemplary embodiment of the present invention.

FIG. 1 depicts Total X-Ray Fluorescence (TXRF) equipment 110 for performing surface concentration measurements. TXRF equipment 110 is calibrated by performing a measurement (in TXRF calibration mode 112) on a reference standard sample 120 which includes a target element 121 and a radioactive marker element 122 in known (or measured) ratio. Because radioactive marker element 122 decays at a known rate, i.e., because radioactive marker element 122 decays in accordance with a known half-life, $T_{1/2}$, a measurement (in marker element count mode 111) of the flux of radioactive decay products of radioactive marker element 122 is indicative of the number of atoms of radioactive marker element 122 included on reference standard sample 120 at a particular time in its decay history (or future). Using a known (or measured) ratio of target element 121 to radioactive marker element 122, a system, composition, or method in accordance with the present invention parlays a measured number of atoms of radioactive marker element 122 into an otherwise unknown number of target element 121 atoms included on reference standard sample 120.

The flux of X-rays received at X-ray detector 130 of TXRF equipment 110 from reference standard sample 120 (during TXRF calibration mode 112) is then calibrated against the known number of atoms of target element 121 (and of radioactive marker element 122, if significant). Variations on the analytic technique, which depend on the relative populations of target element 121 and radioactive marker element 122, on the particular target and marker elements chosen, and on the particular techniques used for measurement of radioactive decay products and of the $N_{target}:N_{marker}$ ratio, are described below.

In general TXRF equipment 110 operates as follows. When a specimen is irradiated with X-rays, fluorescence X-rays of characteristic energy to the elements that constitute the specimen are generated. The intensities of the fluorescence X-rays are proportional to the amounts of the corresponding elements. Geometric configurations which result in total reflection of the incident X-rays on the specimen reduce the intensity of the scattered X-rays and also help to localize the generation of fluorescence X-rays to near surface layers of the specimen. In this way, a spectrum of fluorescence X-ray with a large signal-to-background ratio can be obtained. Detection limits of such TXRF equipment depend on the atomic numbers and excitation energies of elements on the surface of the specimen and on photon flux and energy bandwidth of excitation X-rays, background noise, integration time, etc. Persons of ordinary skill in the art will recognize a wide variety of suitable TXRF configurations and operating parameters. See e.g., *Third Working Daft, Surface chemical analysis—Determination of contamination elements contents on silicone wafer—Total reflections X-ray fluorescence spectroscopy (TXRF)*, ISO/TC 201/WG2 N 26, Nov. 28, 1995 (specifying TXRF configurations and methods for surface concentration measurements on polished and epitaxial silicon wafer surfaces).

In an exemplary embodiment of the present invention, reference standard sample 120 includes iron in its most abundant form (Fe-56) as target element 121 and a radioactive isotope of iron (Fe-55) as radioactive marker element 122. Fe-55 has a half-life of approximately 2.6 years which is long enough to provide a useful reference standard lifetime, but short enough so that there are a sufficient number of decay products per second available for sampling from a relatively small number of Fe-55 atoms. Furthermore, Fe-55 decays via electron capture, yielding relatively low energy X-rays that require no additional shielding for personnel safety and are readily detectable by the same X-ray detector 130 as used for concentration measurements.

In the exemplary embodiment of FIG. 1, the ratio of Fe-56 to Fe-55, i.e., $N_{Fe-56}:N_{Fe-55}$, is measured by Time Of Flight-Secondary Ion Mass Spectroscopy (TOF-SIMS), using equipment such as Time Of Flight-Secondary Ion Mass Spectrometer (TOF-SIMS) 171. Since TOF-SIMS is a destructive analytic technique, the ratio measurement is performed on one 120a of plural reference standard samples prepared from the same certified stock solutions as used for preparation of reference standard sample 120 for use in TXRF calibration mode 112. In this way, the reference standard sample consumed by TOF-SIMS analysis (i.e., reference standard sample 120a) is substantially identical that used directly in TXRF calibration. Alternatively, a ratio measurement by TOF-SIMS may be performed after TXRF decay product X-ray measurements, thereby mitigating the consumption of reference standard sample 120. In either case, secondary ions 172 (from target element 121a and radioactive marker element 122a) are sputtered off the surface of reference standard sample 120a by ion source 173 and are separated out by TOF-SIMS 171 into a signal (or signals) 182 associated with the incidence of target element 121 and radioactive marker element 122 among the secondary ions 172. TOF-SIMS 171 need not be calibrated for surface concentrations levels such those presented by reference standard sample 120a, since the mere ratio of target element 121 to radioactive marker element 122 is robust to an uncalibrated response. After processing by data/signal processor 161, signal 182 is transformed into $N_{target}:N_{marker}$ ratio data 162 (i.e., into $N_{Fe-56}:N_{Fe-55}$ ratio data).

Alternatively, a desired $N_{Fe-56}:N_{Fe-55}$ ratio can be established by precisely combining certified stock solutions of the two isotopes. Using wet chemistry such as volumetric techniques with calibrated pipettes, reference standard samples such as reference standard sample 120 can be reliably prepared in known ratio with Fe-55 concentrations on the order of $10^7$ atoms/cm$^2$. A variety of suitable alternative techniques and apparats for measuring the $N_{Fe-56}:N_{Fe-55}$ ratio will also be apparent to persons of ordinary skill in the art. For example, Inductively Coupled Plasma-Mass Spectrometry (ICP/MS), Isotope Dilution Mass Spectrometry, etc. are all suitable. Ratio measurement is by any such suitable technique, using any such suitable apparatus, and provides $N_{target}:N_{marker}$ ratio data 162.

TXRF equipment 110 includes X-ray detector 130, which, in marker element count mode 111, detects decay product X-rays 151 from the radioactive decay of Fe-55. An X-ray incidence signal 181 corresponding to the flux of decay product X-rays 151, typically in counts per second, is supplied from X-ray detector 130 to data/signal processor 166. Data/signal processor 166 in turn computes and supplies Fe-55 count data 163, which, in the exemplary Fe-56/Fe-55 embodiment described above is Fe-55 count data. Suitable techniques for deriving a radioactive element count from an X-ray incidence signal, such as X-ray incidence signal 181, are well known to persons of ordinary skill in the art. Data/signal processor 166 implements any such suitable techniques.

Given the solid angle subtended by the X-ray detector 130, the efficiency of X-ray detector 130, and the number of decay product X-rays per decaying atom of radioactive marker element 122, a measurement of the number of decay products emitted (i.e., X-ray incidence signal 181) yields the time rate of change for the number of radioactive marker element atoms, or $dN(t)/dt$ where $N(t)$ is the number of undecayed atoms at a given time t.

In general, for atoms that decay directly to a stable isotope, the number of undecayed atoms is given by:

$$N(t)=N_0 e^{-Rt},$$

where $N_0$ is the number of undecayed atoms at t=0 (i.e., the approximate time at which the ratio measurement is made) and R is the decay rate which can be expressed in terms of the half-life $T_{1/2}$ as $R=\ln(2)/T_{1/2}$. Taking the time derivative of the decay equation and solving for $N_o$ one finds that:

$$N_0 = \frac{-e^{Rt}}{R}\frac{dN(t)}{dt}.$$

Thus, with the derivation of $dN(t)/dt$ from X-ray incidence signal 181, with a known half-life, $T_{1/2}$, for the radioactive marker element 122 (approximately 2.6 years for Fe-55), and with the time, t, since ratio measurement 170 was made, one can determine the number of radioactive marker element atoms 122 originally present in reference standard sample 120. In the exemplary embodiment of FIG. 1, data/signal processor 166 performs such a determination and results thereof are represented as marker element count data 163.

The number (or concentration) of target element 121 atoms on reference standard sample 120 is calculated by data/signal processor 164 based on the number of undecayed radioactive marker element 122 atoms originally present in reference standard sample 120 (calculated as described above with reference to data/signal processor 166) and the previously measured ratio, $N_{target}:N_{marker}$. For example, if $N_{0, Fe-55}$ is determined to be $10^7$ atoms/cm$^2$ and the measured ratio of target element 121 atoms to radioactive marker element 122 atoms, $N_{Fe-56}:N_{Fe-55}$, is 1000/1, then the concentration of target element 121 atoms present on reference standard sample 120 is $10^{10}$ atoms/cm$^2$.

In TXRF calibration mode 112, the flux of fluorescence X-rays 152 detected from reference standard sample 120 by X-ray detector 130 (signal 183) is calibrated to the calculated concentration of target element 121 (and of radioactive marker element 122, if significant). For example, a TXRF scan of reference standard sample 120 (discussed above) might yield 100 counts per second per square centimeter (cps/cm$^2$) when scanning for Fe atoms. If, as described above, reference standard sample 120 is determined to include $10^{10}$ target element 121 atoms/cm$^2$, a subsequent scan for Fe on an unknown sample that yields 50 cps/cm$^2$ corresponds to a concentration of $5 \times 10^9$ atoms/cm$^2$. For large ratios of $N_{Fe-56}:N_{Fe-55}$, virtually all of signal 183 is from fluorescing Fe-56 atoms and $N_{Fe}:N_{Fe-55} \sim N_{Fe-56}:N_{Fe-55}$. Both the fluorescence X-ray and decay product X-ray contributions from the marker isotope to the total incidence of X-rays at X-ray detector 130 are negligible and may be ignored. However, if desired or in alternative embodiments with smaller $N_{target}:N_{marker}$ ratio, these additional X-ray contributions may be included in the analysis implemented by data/signal processor 164. Calibration methods, including methods for extrapolating a calibration for a particular element, e.g., target element 121, to other elements of interest are well known in the art. For example, relative sensitivity factors allow a calibration for a particular element (typically Fe or Ni) to be parlayed into calibrations for other elements of interest. Methods for determining such relative sensitivity factors are well known to persons of ordinary skill in the art. See e.g., ANNEX B, *Third Working Draft, Surface chemical analysis—Determination of contamination elements contents on silicone wafer—Total reflections X-ray fluorescence spectroscopy (TXRF)*, ISO/TC 201/WG2 N 26, Nov. 28, 1995. Data/signal processor 164 implements any such suitable calibration methods.

FIG. 1 includes an exemplary decomposition of computations for processing raw signals from TOF-SIMS 171 and TXRF equipment 110 to produce calibration data 165 for use in low-level concentration measurements. Persons of ordinary skill in the art will recognized a large variety of suitable alternative decompositions of calibration computations. For example, much of the signal processing may be provided by hardware or software provided as part of a data acquisition and control interface to measurement equipment. Additionally, computations to arrive at calibration data do not necessarily require a physically connected system. Therefore, computations for determining calibration data 165 may be completed manually and raw count per second measurements from TXRF equipment 110 may be adjusted manually in accordance with the calibration data 165. Similarly, the functionality of one or more of data/signal processor 161, data/signal processor 166, and data/signal processor 164, together with intermediate target to marker ratio data 162 and marker element count data 163 representations may be combined to implement a calibration subsystem in hardware and or software.

Although one presently preferred embodiment of reference standard sample 120 includes Fe as target element 121 and Fe-55 as radioactive marker element 122 at an $N_{Fe}:N_{Fe-55}$ ratio of approximately 1000:1, alternative embodiments including other element combinations and element ratios are also suitable.

In general, target element 121 should be detectable by the concentration measurement technique (e.g., TXRF, TOF-SIMS, etc.) that is being calibrated and radioactive marker element 122 should be chosen based on factors including:

1. radioactive decay into relatively low energy decay products so as not to pose a threat to personnel or processing equipment and not to require additional shielding;
2. radioactive decay into decay products that are relatively easy to detect by either the concentration measurement apparatus itself or alternate readily available equipment; and
3. a radioactive decay rate sufficiently low to ensure reference standard longevity yet sufficiently high to insure an adequate count rate for determining the number of radioactive atoms present on the reference standard.

In addition, when, as in a presently preferred embodiment, radioactive marker element 122 is a radioactive isotope of target element 121, chemistry steps necessary to produce reference standard sample 120 are identical for both the radioactive marker and target elements. This provides a more reliable ratio since, in such a case, the $N_{target}:N_{marker}$ ratio in reference standard sample 120 is the same as that of the liquid stock solution.

A presently-preferred embodiment including Fe as target element 121 and one of iron's radioactive isotopes (Fe-55) as the radioactive marker element 122 has several of advantages. First, Fe is a common impurity found in semiconductor processing and consequently it is often the subject of surface concentration analysis. Second, Fe binds tightly with a silicon wafer substrate thereby insuring that Fe deposited on a wafer as part of a reference standard will remain there for the useful life of the reference standard. Fe-55 has a half-life of approximately 2.6 years which is long enough to provide a usefull reference standard lifetime, but short enough so that there are sufficient decay events per second from a relatively small number of atoms to provide a well-behaved, easily-measured fux of decay products. Furthermore, Fe-55 decays via electron capture, yielding relatively low energy X-rays that require no additional shielding and are readily detectable by the same TXRF apparatus used for concentration measurements.

In general, a search set for suitable target element 121 instances is defined by the set of elements detectable by a measurement device to be calibrated. A target element near the middle of a measurement device detection window is desirable, though not essential. The search set for suitable radioactive marker element 122 instances is defined by the set of isotopes for which detectable decay products exist. Although a presently preferred embodiment includes a radioactive isotope of the target element (i.e., includes Fe and Fe-55), target element 121 and radioactive marker element 122 need not be isotopes of the same element. For example, a reference standard sample 120 including Fe-55 as the radioactive marker element 122 and Ni as the target element 121 is also suitable. The main complicating factor is deposition from stock solutions to form reference standard sample 120. Since Ni and Fe can deposit out of the stock solution at different rates, the ratio of Ni:Fe-55 in such an embodiment of reference standard sample 120 may not be the same as that of the stock solution. However, this ratio can be measured using TOF-SIMS as described earlier. In this context, any element with Z between 15 and 30, i.e., any element detectable by a typical TXRF apparatus, is a suitable target element. For an advanced TXRF apparatus capable of fluorescing L-lines or M-lines (rather than K-lines), high Z elements would also be suitable. An identity of decay products of radioactive marker element 122 and the target element 121 signature measured by the particular measurement device to be calibrated is unnecessary, though convenient.

In one alternative embodiment, target element 121 is Mn-55 and radioactive marker element 122 is Mn-56. Unfortunately, since the half life of Mn-55 is approximately 2½ hours, the usefull life of a reference standard sample 120 prepared with Mn-55 as radioactive marker element 122 is limited. Such a reference standard sample 120 has a useful life of only a few days, as compared with the approximately 5 year useful life of a presently preferred Fe/Fe-55 embodiment. Mn-54 has a half-life (315 days) more suitable for a longer reference standard lifetime; however, its decay product includes a high energy γ-ray. Although alternatives to the exemplary embodiment of FIG. 1 may count γ-rays, rather than X-rays, and γ-ray decay as an radioactive marker element 122 count indicator is entirely compatible with the calibration technique described herein, γ-ray emissions create substantial personnel safety issues not presented by a presently preferred Fe/Fe-55 embodiment. Other suitable pairs of target element 121 and radioactive marker element 122 include Cr/Cr-51, Sc/Sc46, Ca/Ca45, etc.

Suitable ratios of target element 121 to radioactive marker element 122 are driven by several considerations. In general, lower ratios allow greater precision because the leverage on a precise radioactive decay product measurement is lower. Nonetheless, practical consideration result in a present preference for $N_{target}:N_{marker}$ ratios on the order of 1000:1. In particular, higher ratios reduce the overall flux of decay products and effectively eliminate decay products and other detectable emissions of radioactive marker element 122 from a target element signature such as signal 183. A reduced flux of decay products simplifies radiation hazard issues and licensing requirements, and effective elimination of radioactive marker element 122 contributions from signal 183 allows calibration to ignore decay products and other detectable emissions of radioactive marker element 122. For combinations of target and radioactive marker elements and measurement devices, e.g., TXRF of Fe/Fe-55, which fail to distinguish between isotopes of the same element, this can be a usefull simplification. For example, in the case of TXRF of an Fe/Fe-55 reference standard sample, decay product and fluorescence X-rays from the Fe-55 radioactive marker can reasonably be ignored in TXRF calibration mode 112. Nonetheless, suitable modifications to account for decay products and other detectable emissions of radioactive marker element 122 and to address radiation hazard issues will be apparent to persons of ordinary skill in the art.

The choice of radioactive marker element 122 also affects the desired $N_{target}:N_{marker}$ ratio. In particular, a radioactive marker element 122 having a longer half-life will, for a particular $N_{marker}$, generate a smaller flux of detectable decay products as compared with a radioactive marker element 122 having an shorter half-life. Depending on the signal-to-noise ratio and statistics of the resulting decay product signal (illustratively, X-ray incidence signal 181), $N_{marker}$ may need to be increased (and correspondingly $N_{target}:N_{marker}$ decreased) for a particular radioactive marker element 122.

Alternative embodiments may address the shielding and licensing issues raised by a high flux of decay products and may consider decay product and other detectable emission contributions to an apparent target element signature such as signal 183. Suitable shielding designs and mathematical treatments for these additional contributions will be apparent to persons of ordinary skill in the art. In such alternative embodiments, the $N_{target}:N_{marker}$ ratio will be driven by a tradeoff between desired precision of calibration and the magnitude of the shielding and licensing task At an extreme end of a range of such variations in $N_{target}:N_{marker}$ ratio, a single isotope reference standard, in which the single isotope functions both as the calibration target and the radioactive marker, is also possible. One such single isotope reference standard is described in greater detail in a co-pending patent application entitled, "Ultra-Low-Level Standard for TXRF," Application Ser. No. 08/712,715, now U.S. Pat. No. 5,841, 016 naming Hossain et al. as inventors and filed on even date herewith, the entirety of which is hereby incorporated by reference.

Whatever the particular combination of target element 121 and radioactive marker element 122, and whatever the desired $N_{target}:N_{marker}$ ratio, a small amount of the reference standard material is deposited on the surface of a clean substrate typical of those used for concentration measurements, e.g., in the case of a TXRF measurement, a <100> oriented silicon wafer. Deposition can be accomplished by a variety of techniques including spin-coating, wafer immersion, and vapor-phase deposition. In one presently preferred embodiment, a microdroplet of the reference standard material is deposited onto the center of a silicon wafer and then dried under controlled environmental conditions.

Figure 2:
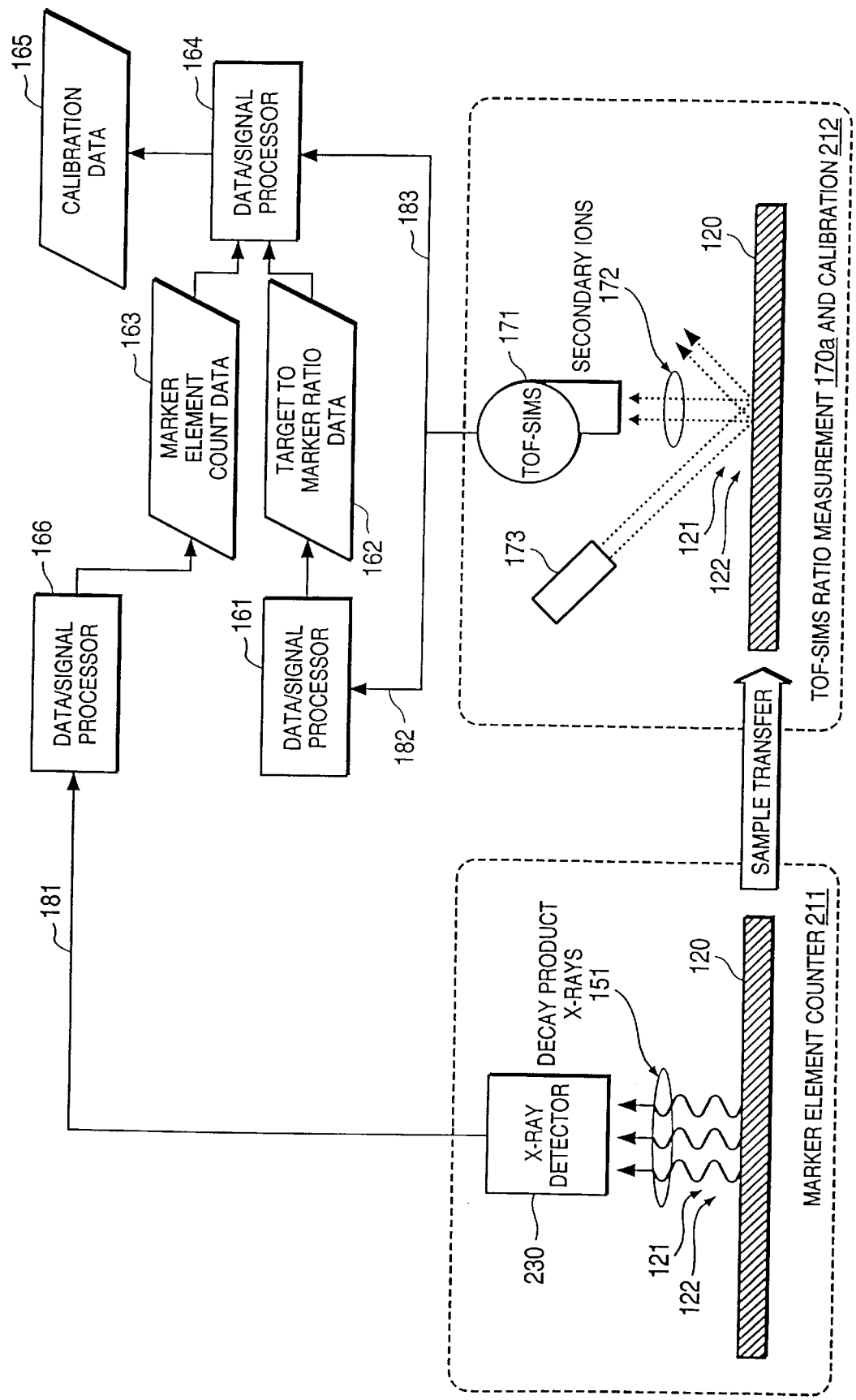
FIG. 2 depicts a system, apparatus, and method for calibrating a Time Of Flight-Secondary Ion Mass Spectrograph (TOF-SIMS) apparatus for low-level surface concentration measurements using a reference standard sample in accordance with an exemplary embodiment of the present invention.

FIG. 2 depicts an alternative Time Of Flight-Secondary Ion Mass Spectroscopy (TOF-SIMS) embodiment in which TOF-SIMS 171 (rather than a TXRF measurement) is calibrated for low-level concentration measurements in accordance with the present invention. As before, an X-ray detector 230 detects decay product X-rays 151 from radioactive marker element 122 on reference standard sample 120. X-ray incidence signal 181 is processed by data/signal processor 166 to provide marker element count data 163. Reference standard sample 120 is transferred to TOF-SIMS 171 for ratio measurement and for the actual calibration. As before, TOF-SIMS is used to determine the $N_{target}:N_{marker}$, ratio for reference standard sample 120. However, in the embodiment of FIG. 2, signal 182 including counts for target element 121 and radioactive marker element 122 (for ratio calculation) and signal 183 including a count for target element 121 are generated as part of the same measurement of secondary ions 172.

In the embodiment of FIG. 2, decay product detection at marker element counter 211 and ratio/calibration measurements at TOF-SIMS 171 are performed in sequence at approximately the same time so that intertemporal decay of radioactive marker element 122 is insignificant. Alternatively, either the mathematical manipulations associated with data/signal processor 166 or data/signal processor 161 can be modified to accurately represent the time lag between decay product measurement and ratio measurement Suitable modifications based on the decay equations described above will be apparent to persons of ordinary skill in the art Decay product X-rays 151 are detected by an X-ray detector 230, typically a Si(Li) detector similar to that used in TXRF equipment 110. However, a variety of suitable alternative embodiments for marker element counter 211 will be appreciated by persons of ordinary skill in the art In particular, in one such suitable alternative, the decay product X-ray measurement is performed using a well characterized X-ray detector 230 at a research laboratory such as the National Institute of Standards and Technology, NIST, and supplied as radioactive marker element 122 count (or concentration) at a particular time. TOF-SIMS 171 is then calibrated as described above using the supplied radioactive marker element 122 count as marker element count data 163.

Figure 3:
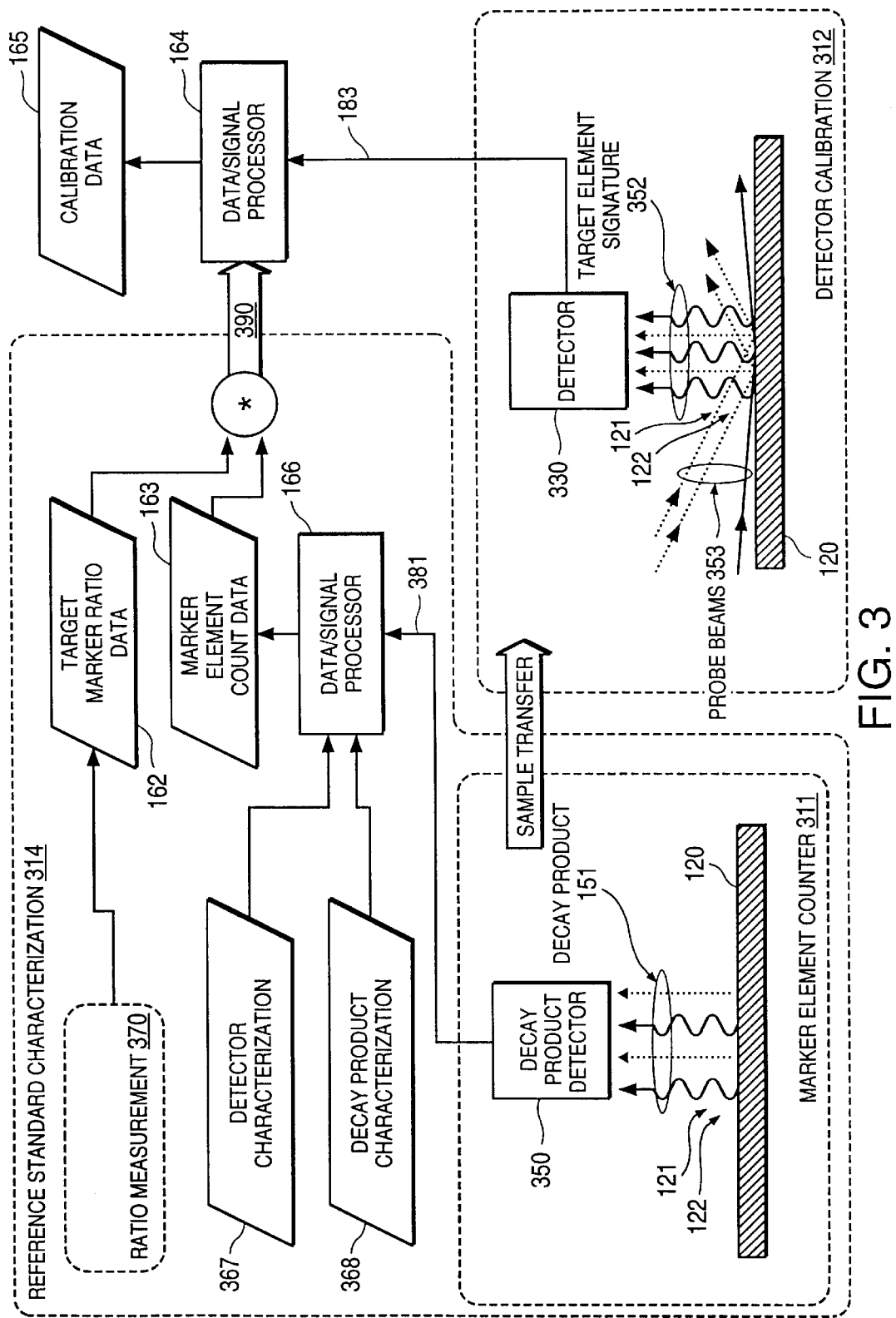
FIG. 3 depicts a system, apparatus, and method for characterizing the target element concentration of a reference standard sample and providing the reference standard sample so characterized for calibration of a target element detector apparatus in accordance with an exemplary embodiment of the present invention.

FIG. 3 depicts yet another alternative embodiment in which a characterized reference standard sample 120 including characterized numbers (or concentrations) of target element 121 and radioactive marker element 122 are used in detector calibration 312. Detector 350 detects target element 121 signature 352 which is generated under excitation from probe beams 353. Detector 350 is representative of detectors for a wide variety of concentration measurement techniques, including TXRF, TOF-SIMS, XRF, SIMS, AES, RBS, etc. As before, the embodiment of FIG. 3 builds on a measurement of decay products from radioactive marker element 122 and a measurement of the $N_{target}$:$N_{marker}$ ratio for reference standard sample 120. Marker element counter 311 includes a decay product detector 330, which in various alternative embodiments detects X-rays, γ-rays, β particles, α-particles, etc. In a presently preferred embodiment, radioactive marker element 122 emits low-energy X-rays and decay product detector 330 is an X-ray detector, although decay products of varying energies, masses, and other characteristics are also possible. Suitable detector designs and shielding requirements will be appreciated by persons of ordinary skill in the art.

Reference standard characterization 314 is potentially performed off-site of the eventual detector calibration 312. In one such embodiment, a target element count 390 is computed from its precursors, ratio measurement 370 and X-ray incidence signal 181. Reference standard sample 120 is then supplied with target element count 390 as a characterized reference standard for use in calibration of detector 330 (e.g., X-ray detector 130, TOF-SIMS 171, etc.). For calibration of measurements which are insensitive to the differences between target element 121 and radioactive marker element 122, a count of radioactive marker element 122 can optionally be supplied so that calibration of detector signal 183 can consider decay product and/or stimulated emission contributions from radioactive marker element 122 to target element signature 352. For example, in the case of Fe/Fe-55 TXRF embodiments previously described, both decay product and fluorescence X-rays from Fe-55 contribute, though only marginally, to an apparent Fe X-ray fluorescence signature (i.e., fluorescence X-rays 152). In such an embodiment, particularly one with a $N_{target}$:$N_{marker}$<1000:1, a count of radioactive marker element 122 allows calibration at data/signal processor 164 to consider the decay product and fluorescence X-ray contributions from the Fe-55 radioactive marker.

The particular marker element counter 311 configuration depends on the type of radioactive decay product emitted by the radioactive marker element 122. In the case of Fe-55, which emits X-rays, a presently preferred radioactive decay product measuring technique is to use the X-ray detector built into a TXRF apparatus. This avoids the use of a second apparatus and allows the concentration measurement calibration and the radioactive element measurement to be made in rapid succession without removing the reference standard. For alternative embodiments in which radioactive marker element 122 decays producing other decay products, marker element counter 311 is a corresponding decay product detector.

In a set of alternative embodiments of reference standard sample 120, of systems, methods, and apparats for use of reference standard sample 120, and of methods for characterizing reference standard sample 120, radioactive marker element 122 is a short-lived radioisotope. Although radioactive marker element 122 is rapidly depleted and radioactive decay products therefrom quickly become negligible, such an embodiment, if characterized during the short window during which levels of decay products are sufficient for reliable detection, has the advantage of being essentially radiation-free shortly after characterization. As before, the ratio of target element 121 to radioactive marker element 122 is measured using mass spectroscopy (e.g., TOF-SIMS) and the number of radioactive marker element 122 atoms is established using a measured flux of radioactive decay products in conjunction with radioactive decay equations. As before, given a known ratio and a known number of radioactive marker element 122 atoms, the number of target element 121 atoms can be established. Since target element 121 is stable, the number of target element 121 atoms is static (barring subsequent contamination) and may be supplied as a characterization of reference standard sample 120 for use in calibration of concentration measurement devices.

Although other previously described embodiments of the present invention preferably include radioactive marker element 122 selections having half-lives suitable for producing a measurable flux of radioactive decay products for at least several weeks, if not several years, the alternative embodiment now described includes radioactive marker element 122 selections preferably having half-lives ranging from 1–2 hours to 5–10 days. Ratio measurement and radioactive decay product measurements are performed within a period of several half-lives, preferably within one half-life of each other. The target element 121 to radioactive marker element 122 ratio can also be established in accordance with the chemistry of certified stock solutions; however, due to the rapid depletion of radioactive marker element 122 atoms, actual measurement is preferable. After measurements are performed, radioactive marker element 122 atoms on reference standard sample 120 are allowed to decay for approximately 10 half-lives so that residual radioactivity is virtually non-existent. The radioactively depleted material is then released with a certified number of target element 121 atoms for calibration of concentration measurement apparats in accordance with a portion of FIG. 3.

Half-lives required for suitable radioactive marker element 122 selections are such that both ratio measurement 370, e.g., by TOF-SIMS, and decay product measurement, e.g., by decay product detector 350, can be made conveniently before radioactivity decays to a negligible level. For laboratories having both radioactive decay product measurement and ratio measurement capabilities, half-lives of even a few hours are suitable. On the other hand, if either the radioactive decay product measurement or ratio measurement must be performed off-site of the other, a longer half-life of a few days is typically necessary to allow for transportation of reference standard sample 120. Suitable combinations of target element 121 and radioactive marker element 122 include: K and K-42 (half-life 12.36 hours), Ca and Ca-47 (4.54 days), Sc and Sc-47 (3.34 days), Mn and Mn-56 (2.6 hours), Ni and Ni-65 (2.52 hours), Cu and Cu-64 (1.27 hours), and Zn and Zn-69 (13.8 hours). The above list is merely illustrative of suitable selections for target element 121 and radioactive marker element 122 and is not meant to be exhaustive. In general, suitable radioisotopes for radioactive marker element 122 will have a half-life ranging from 1–2 hours to 5–10 days. Persons of ordinary skill in the art will appreciate a wide variety of alternative combinations. As before, target element 121 and radioactive marker element 122 need not be isotopes of the same element. However, for simplicity of wet chemistry (e.g., to eliminate problems associated with different deposition rates out of solution), radioactive marker element 122 is preferably a radioactive isotope of target element 121.

Preferably, for personnel safety during reference standard sample 120 characterization, radioactive decay products of radioactive marker element 122 are limited to X-rays or β-particles. However, because more dangerous decay products (e.g., γ-rays and α-particles) will be reduced to negligible levels after a short period of time, radioactive marker element 122 selections decaying thereby may also be suitable for use with adequate precautions under controlled laboratory conditions. Suitable shielding and other personnel safety precautions will be appreciated by persons of ordinary skill in the art.

While the invention has been described with reference to various embodiments, it will be understood that these embodiments are illustrative and that the scope of the invention is not limited to them. Many variations, modifications, additions, and improvements of the embodiments described are possible. For example, a broad range of selections for target element 121 and radioactive marker element 122 and ratios therebetween are possible. Target element 121 and radioactive marker element 122 may be isotopes of the same element, may be isotopes of different elements, or may be the same isotope of the same element In addition, radioactive marker elements having non-X-ray decay products are possible with corresponding modifications to a marker element counter. A wide variety of measurement techniques are possible for establishing a $N_{target}$: $N_{marker}$ ratio and for counting decay products of radioactive marker element 122. With respect to the system and method embodiments, the data/signal processing configuration described herein is merely illustrative. Alternative embodiments of systems and methods for calibrating a concentration measurement device may incorporate manual or automated processes or a combination of manual and automated processes. The particular description herein of computations and intermediate data is similarly illustrative. Alternate configurations and implementations of the underlying computations are also possible. Additionally, a wide variety of concentration measurement techniques may be calibrated using systems, compositions, and methods in accordance with the present invention. These and other variations, modifications, additions, and improvements may fall within the scope of the invention as defined in the claims which follow.

What is claimed is:

1. A reference standard material for calibrating a concentration measurement apparatus, the reference standard material comprising:

a substrate;

a first amount of a target element detectable by the concentration measurement apparatus and on the substrate; and a second amount of a radioactive marker element combined with the target element on the substrate in known ratio.

2. A reference standard material, as recited in claim 1, wherein the substrate comprises a Si wafer.

3. A reference standard material, as recited in claim 1, wherein a flux of decay products of the radioactive marker element provides a precise indication of a number of atoms of the radioactive marker element on the substrate.

4. A reference standard material, as recited in claim 1, wherein radioactive decay products of the radioactive marker element are substantially limited to X-rays.

5. A reference standard material, as recited in claim 1, wherein the target element and the radioactive marker element respectively comprise a substantially non-radioactive isotope and a radioactive isotope of the same element.

6. A reference standard material, as recited in claim 1, wherein the target element is a substantially non-radioactive isotope of a first element, and wherein the marker element is a radioactive isotope of a second element.

7. A reference standard material, as recited in claim 1, wherein the radioactive marker element is Fe-55.

8. A reference standard material, as recited in claim 1, wherein the target element is Fe and the radioactive marker element is Fe-55.

9. A reference standard material, as recited in claim 1, wherein the target element is Fe-56 and the radioactive marker element is Fe-55.

10. A reference standard material, as recited in claim 1, wherein the target element is Ni and the radioactive marker element is Fe-55.

11. A reference standard material, as recited in claim 1, wherein the radioactive marker element is selected from the set of Mn-56, Cr-51, Sc-46, and Ca-45.

12. A reference standard material, as recited in claim 1, wherein the first amount of the target element is much greater than the second amount of the radioactive marker element.

13. A reference standard material, as recited in claim 1, wherein the known ratio is approximately 1000:1.

14. A reference standard material, as recited in claim 1, wherein a half-life of the radioactive marker element and the second amount thereof are such that a flux of decay products impinging on a detector therefor is reliably measurable to a precision of one part in one hundred.

15. A reference standard material, as recited in claim 1, wherein a half-life of the radioactive marker element is longer than a week and shorter than ten years.

16. A reference standard material, as recited in claim 1, wherein a half-life of the radioactive marker element is longer than one year and shorter than five years.

17. A reference standard material, as recited in claim 1, wherein a half-life of the radioactive marker element is longer than two years and shorter than three years.

18. A reference standard material, as recited in claim 1,
   wherein a half-life of the radioactive marker element and the second amount thereof are sufficient for measurement, within a several half-life interval, of a flux of radioactive decay products therefrom and of the known ratio; and
   wherein after approximately ten half-lives, residual radioactivity from undecayed atoms of the radioactive marker element is negligible.

19. A reference standard material, as recited in claim 1, wherein a half-life of the radioactive marker element is longer than approximately 1 hour and shorter than approximately 10 days.

20. A reference standard material, as recited in claim 1, wherein a half-life of the radioactive marker element is approximately 1–2 hours.

21. A reference standard material, as recited in claim 1, wherein a half-life of the radioactive marker element is approximately 5–10 days.

22. A reference standard material, as recited in claim 1, wherein radioactive decay products of the radioactive marker element are substantially limited to radioactive decay products of a type and flux for which for which shielding is substantially unnecessary for personnel safety.

23. A reference standard material, as recited in claim 1,
   wherein radioactive decay products of the radioactive element are substantially limited to X-rays; and
   wherein the half-life of the radioactive element is such that radioactive decay induced change in the ratio of the first amount to the second amount is substantially negligible for a period of approximately one year; and wherein the half-life of the radioactive element is such that a flux of X-ray decay products impinging on an X-ray detector is reliably measurable to a precision of one part in one hundred.

24. A reference standard material, as recited in claim 1, wherein the known ratio of the first amount to the second amount is characterized using a Time Of Flight-Secondary Ion Mass Spectrometer (TOF-SIMS) apparatus.

25. A reference standard material, as recited in claim 1, wherein the known ratio of the first amount to the second amount is established by preparation from certified stock solution.

* * * * *

UNITED STATES PATENT AND TRADEMARK OFFICE
CERTIFICATE OF CORRECTION

PATENT NO.   : 6,043,486
DATED        : Mach 28, 2000
INVENTOR(S)  : Hossain, Timothy Z.

It is certified that error appears in the above-identified patent and that said Letters Patent is hereby corrected as shown below:

Column 14,
Line 61, after "for which" delete -- for which --.

Signed and Sealed this

Eighteenth Day of June, 2002

*Attest:*

*Attesting Officer*

JAMES E. ROGAN
*Director of the United States Patent and Trademark Office*